United States Patent [19]

Reuven et al.

[11] Patent Number: 6,136,934
[45] Date of Patent: Oct. 24, 2000

[54] PROCESS FOR MAKING SUBSTANTIALLY HOMOGENEOUS POLYMERS

[75] Inventors: Yakir Reuven, West Orange; Kou-Chang Liu, Wayne, both of N.J.

[73] Assignee: ISP Investments Inc., Wilmington, Del.

[21] Appl. No.: 08/365,384

[22] Filed: Dec. 28, 1994

[51] Int. Cl.[7] ............................ C08F 26/10; C08F 220/10
[52] U.S. Cl. .......................................... 526/264; 526/328.5
[58] Field of Search .................................. 526/264, 328.5

[56] References Cited

U.S. PATENT DOCUMENTS 4,039,734   8/1977   Hendy ...................................... 526/258

*Primary Examiner*—David W. Wu
*Assistant Examiner*—Tanya Zalukaeva
*Attorney, Agent, or Firm*—Walter Katz; William J. Davis; Marilyn J. Maue

[57] ABSTRACT

A process is described for making substantially homogeneous polymers of at least two monomers having substantially differing reactivity rates.

1 Claim, 2 Drawing Sheets

PROCESS FOR MAKING SUBSTANTIALLY HOMOGENEOUS POLYMERS

BACKGROUND OF THE INVENTION

1. Field of the Invention

This invention relates to a process for making substantially homogeneous polymers of at least two monomers having substantially differing reactivity rates.

2. Description of the Prior Art

Synthetic polymers generally are made by a "one-pot" polymerization process in which selected amounts of the several monomers are reacted together. The composition of these one-pot polymers was considered as being the same as the composition of the charged monomers. However, in reality, because of differing reactivity rates of the monomers, such a polymerization process can provide only a mixture of polymers of various compositions, and, additionally, indeterminate amounts of homopolymers and undesired copolymers.

Accordingly, it is an object of this invention to provide a process for making substantially homogeneous polymers of at least two monomers having substantially differing reactivity rates.

IN THE DRAWINGS

DETAILED DESCRIPTION OF THE INVENTION

Figure 1:
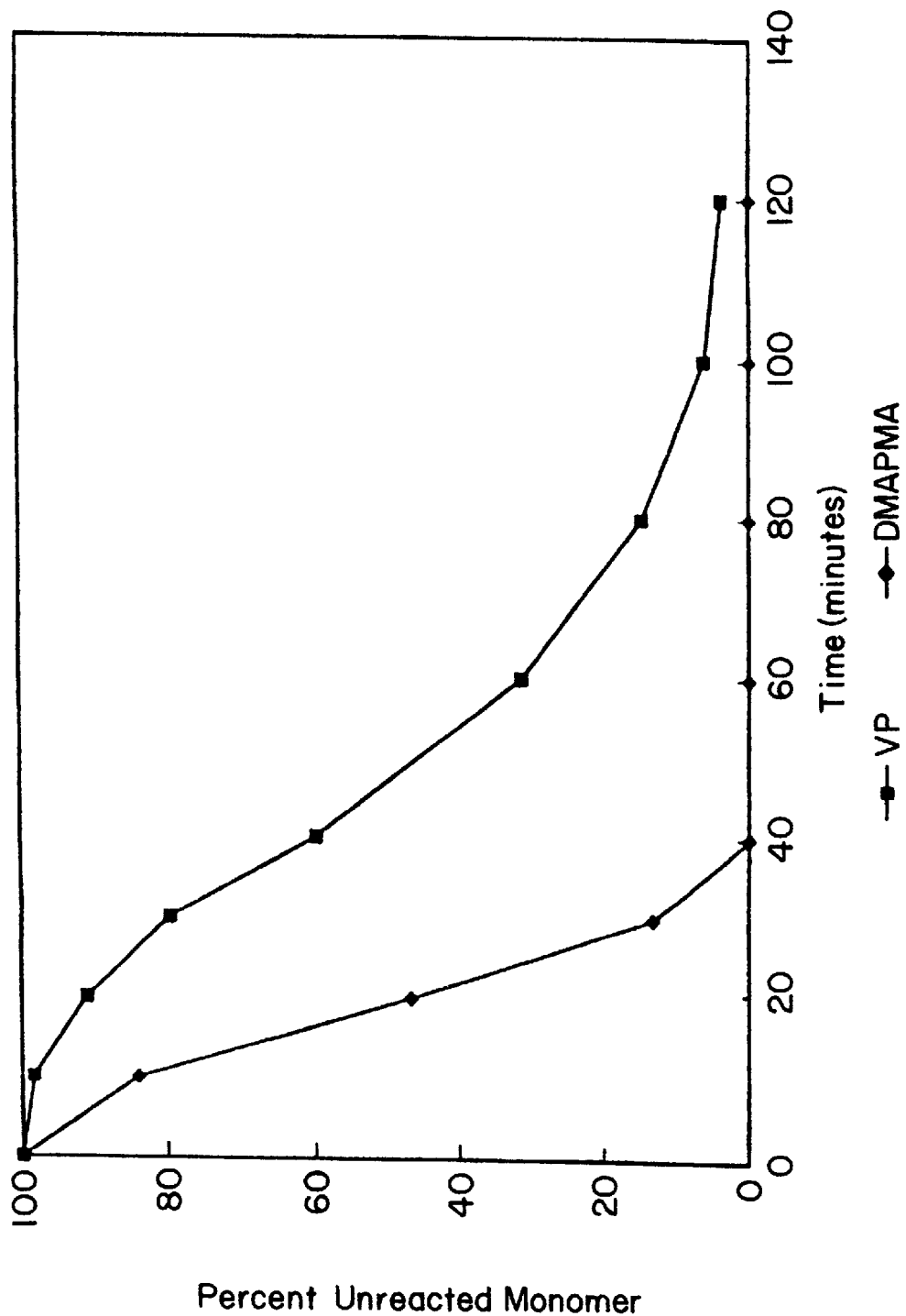
FIG. 1 is a graphical representation of a non-homogeneous (one-pot) polymerization process in which is plotted percent unreacted vinyl pyrrolidone (VP) and N-3,3-dimethylaminopropyl methacrylate (DMAPMA) vs. time for a reaction mixture of 80:20% by weight VP/DMAPMA copolymer at 15% solids.

The invention may be used to prepare homogeneous polymers of any number of monomers as long as one has a slower reactivity rate than the other monomer or monomers in the polymer. The faster reacting monomers are fed incrementally or continuously into a reactor precharged with the slowest reacting monomer.

To illustrate the present invention, a process is provided for making substantially homogeneous copolymers of vinyl pyrrolidone and N-3,3-dimethylaminopropyl methacrylamide of predetermined composition.

In this homogeneous process, the less reactive monomer of the copolymer (VP) is precharged into a reactor at a suitable reaction temperature, generally about 50–80° C., preferably 55–75° C. Then the more reactive monomer (DMAPMA) is introduced incrementally into the VP-charged reactor at a rate which corresponds to the observed rate of disappearance of VP.

The entire predetermined amount of the DMAPMA monomer is added before substantially all the VP monomer has been consumed so that both monomers can react to form a substantially homogeneous copolymer in a desired compositional ratio of VP:DMAPMA. Consequently, a copolymer is obtained whose composition approaches the nominal monomer ratio of the desired copolymer composition and whose structure has the two individual monomeric units of the copolymer distributed substantially uniformly in a homogeneous chain along the backbone of the polymer. For example, for an 80:20 weight ratio of VP/DMAPMA copolymer, which is approximately equivalent to a 6:1 mole ratio of VP/DMAPMA, the homogeneous copolymer of the invention has a monomer distribution corresponding substantially close to VP-VP-VP-VP-VP-VP-DMAPMA-VP-VP-VP-VP-VP-DMAPMA . . .

The precharge in the process of the invention may include some DMAPMA therein, without affecting the homogeneous polymerization process. However, it is still necessary that the rate of addition of DMAPMA after any precharge is carried out at substantially the rate of disappearance of VP during copolymerization.

The schedule of addition of DMAPMA to accomplish the desired matched rate of reaction of VP is determined in the following manner.

DETERMINATION OF ADDITION SCHEDULE FOR DMAPMA TO FORM A HOMOGENEOUS COPOLYMER OF VP AND DMAPMA

A. First, a one-pot copolymerization of VP and DMAPMA was carried out as follows:

EXAMPLE 1

VP (215 g), DMAPMA (54 g), and deionized water (1530 g) were charged into a 2-liter resin pot equipped with a gas inlet, a liquid inlet, a thermometer and a condenser. A stream of nitrogen then was bubbled through the solution and maintained during the reaction. The solution was gradually heated to 68° C.; then 0.25 ml of Lupersol 11 (t-butylperoxy pivalate) as catalyst was added; then another 0.25 ml of the catalyst was added after 10 minutes; and another 6 units of 0.25 ml were added at 30 minute intervals. The total addition was carried out over a 4-hour period.

The relative percentage amounts of residual monomers present during the course of the one-pot reaction was determined by gas chromatographic analysis after sampling the reaction mixture periodically. The analytical data obtained then was plotted as the graph of FIG. 1.

As shown in FIG. 1, DMAPMA reacts much more rapidly than VP. Accordingly, after 240 minutes, all the DMAPMA is consumed while residual VP monomer still is available for homopolymerization. Thus the copolymer formed is of a composition different from the desired monomer ratio selected by the precharged amounts of the two monomers. Under these experimental conditions, the polymer product obtained is a complex mixture of a homopolymer which is polyvinylpyrrolidone, and a copolymer of VP and DMAPMA of uncertain composition.

B. To form a homogeneous copolymer, it is necessary that the curve of rate of conversion vs. time for DMAPMA substantially coincide or match the rate of conversion curve for VP. To accomplish this, the VP is precharged and substantially all the DMAPMA is fed after to the precharge at a feeding schedule determined by analysis of the data of FIG. 1. The % DMAPMA monomer to be fed at time t of the polymerization is determined from the Asymmetric Double Sigmoidal Distribution formula, $A_f$, below, which has four adjustable parameters, $a_1$, $a_2$, $a_3$ and $a_4$:

$$A_t = \cfrac{1}{1 + \exp\left[\cfrac{a_1 - \cfrac{a_2}{2} - t}{a_3}\right]} \left[1 - \cfrac{1}{1 + \exp\left[\cfrac{a_1 + \cfrac{a_2}{2} - t}{a_4}\right]}\right]$$

where t=time in minutes during copolymerization;

$a_1$ is a parameter which determines the center of the distribution;

$a_2$ is a parameter which affects the width of the distribution;

$a_3$ is a parameter which determines the ascending portion of the distribution; and $a_4$ is a parameter which determines the descending portion of the distribution.

$$\% \text{ DMAPMA to be fed at time } t = \frac{A_t}{\sum_{t=0}^{N} A_t} \times 100$$

where N=time when the polymerization is completed.

To match the DMAPMA curve to the VP curve of FIG. 1, an "initial guess" is made for the values of $a_1$, $a_2$, $a_3$ and $a_4$. These values are inserted into the $A_t$ formula and the % DMAPMA to be fed at time t is calculated. Then a polymerization reaction is carried out using this schedule. The resulting % unreacted DMAPMA during this polymerization will probably not match the % unreacted VP at the same time t. If the % unreacted DMAPMA at time t is too large, then the value of $a_3$ (ascendency) in the $A_t$ formula is increased, $a_4$ (descendency) is decreased, $a_1$ (center) is decreased, and $a_2$ (width) is decreased. Conversely, if the initial guess values of $a_1$ through $a_4$ give a reaction rate for DMAPMA which is too fast, then changes in the values of $a_1$ through $a_4$ are made in a direction opposite to those discussed above.

These new values of the parameters are then used to determine a new feeding schedule. Using this feeding schedule, another polymerization is carried out, and the process of adjustment of the parameters described above is repeated.

This process is known as "interative fitting" of data to a curve. After 4 or 5 such iterative fittings, the experimental VP and DMAPMA curves will be matched to a satisfactory degree, as shown in FIG. 2 herein.

Figure 2:
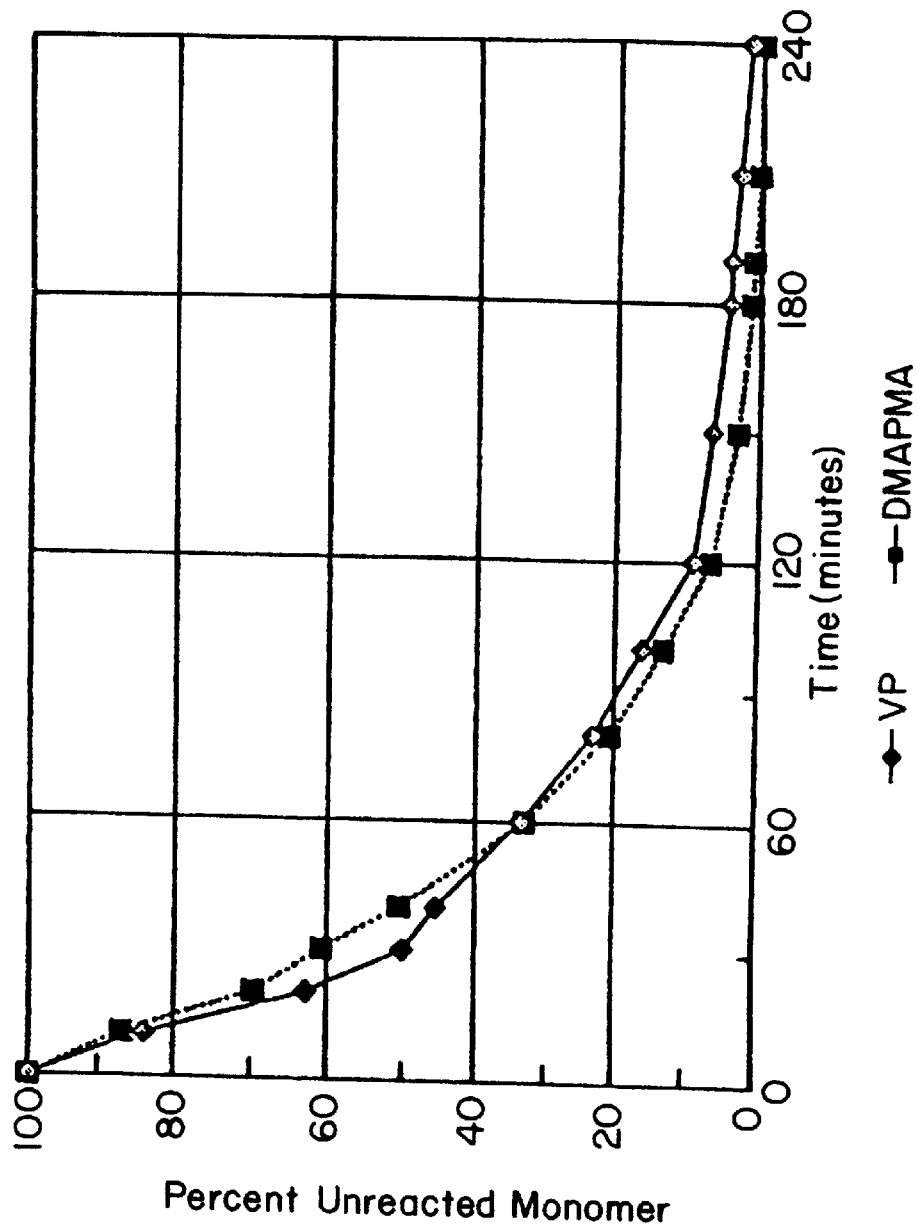
FIG. 2 is a graphical representation of the homogeneous polymerization process of the invention in which is plotted percent unreacted VP and DMAPMA vs. time during the preparation of an aqueous solution of 80:20% by weight VP/DMAPMA copolymer at 15% solids.

The matching curve of DMAPMA in FIG. 2 can originate from at least one set of values for $a_1$, $a_2$, $a_3$ and $a_4$ (the last set of the iterative fitting process) used to calculate a suitable feeding schedule of DMAPMA over the entire period of the polymerization. One such set is:

$a_1$=17
$a_2$=28
$a_3$=2
$a_4$=40

C. With such a suitable DMAPMA feeding schedule available, a homogeneous copolymer of VP and DMAPMA was prepared as described in Example 2 below.

EXAMPLE 2

Preparation of a Homogeneous Copolymer of VP and DMAPMA

In this process, 216 grams of vinylpyrrolidone (recrystallized material) and 580 grams of deionized water were charged to a 2-liter water jacketed resin flask.

The flask was equipped with an overhead stirrer connected to an anchor stirrer, a nitrogen inlet for sparging to remove dissolved air and a thermocouple which is connected to a temperature controller. The temperature was raised to 68° C., by passing heated water from a temperature controlled bath into the jacket of the resin flask. A mechanical syringe pump which could be set to deliver DMAPMA at a set rate was connected to the reactor through polyethylene tubing.

The DMAPMA reactant was added from the syringe pump as a 1 liter solution of 54 grams of DMAPMA in water, according to the following feeding schedule:

| Time (min.) | Amount of DMAPMA Solution Added (ml) |
| --- | --- |
| 0–30 | 418.58 |
| 30-60 | 269.80 |
| 60-90 | 153.90 |
| 90-120 | 80.56 |
| 120-150 | 40.10 |
| 150-180 | 19.38 |
| 180-210 | 9.32 |
| 210-240 | 4.38 |

The totals added during the entire reaction were VP (216 grams), DMAPMA (54 grams) and water (1530 grams).

Additions of Lupersol 11 (t-butyl peroxypivalate, Atochem, NA) initiator were made at various intervals throughout the initial part of the reaction. Additions of 0.25 ml of the initiator were made at 0, 10, 40, 70, 100, 140 and 180 minutes. At 210 and 240 minutes, 0.25 ml of either VAZO 501 (4,4'-azobis(4-cyanovaleric) acid, Wako Pure Chemical Industries, Ltd, Japan) was added to complete the reaction of any residual vinylpyrrolidone monomer. For this purpose, the reaction was allowed to proceed for a total of 10 hours. During this final period the temperature was raised to 75° C. where it was maintained until the reaction was completed.

The product was discharged as a clear, moderately viscous, aqueous solution of a substantially homogeneous copolymer of VP and DMAPMA in an 80:20 weight ratio at a 15% solids level. The residual vinylpyrrolidone content was <0.1%.

The procedure described above can be repeated to provide optimized DMAPMA feeding schedules for any selected copolymer composition, and at any particular solids content, at a prescribed polymerization temperature, solvent level, and amount of initiator.

The invention may be used to prepare homogeneous polymers of any number of monomers as long as one has a slower reactivity rate than the other monomer or monomers in the polymer. The faster reacting monomers are fed incrementally or continuously into a reactor precharged with the slowest reacting monomer.

To summarize this process the entire amount of the slowest reacting monomer is precharged, optionally with some of the faster reacting monomers j, and then the faster reacting monomers are fed incrementally or continuously during the polymerization so that their rates of conversion will match the rate of conversion of the precharged monomer. Specifically the feeding schedule of monomer j is determined from the Asymmetric Double Sigmoidal distribution $A_j$ with four adjustable parameters $a_{1j}$, $a_{2j}$, $a_{3j}$, $a_{4j}$:

$$\text{Percent of monomer } j \text{ charged at time } t_i = 100 \frac{A_j(t_i)}{\sum_{i=0}^{N} A_j(t_i)},$$

where:

$$A_j(t) = \frac{1}{1+\exp\left[\frac{a_{1j} - \frac{a_{2j}}{2} - t}{a_{3j}}\right]} \left[1 - \frac{1}{1+\exp\left[\frac{a_{1j} + \frac{a_{2j}}{2} - t}{a_{4j}}\right]}\right].$$

In the above equations $t_i$ is the time (in minutes) calculated from the beginning of the polymerization reaction, N is the overall time of the polymerization reaction, $a_1$ is a parameter that determines the center of the distribution, $a_2$ determines the overall width of the distribution, $a_3$ determines the ascending part of the distribution and $a_4$ determines the descending part of the distribution.

Each monomer j has its own four $a_j$ parameter values, which determine its specific feeding rate, according to the above equations.

While the invention has been described with particular reference to certain embodiments thereof, it will be understood that changes and modifications may be made which are within the skill of the art. Accordingly, it is intended to be bound only by the following claims, in which:

What is claimed is:

1. A process for making substantially homogeneous polymers of at least two monomers having substantially differing reactivity rates, in a selected composition, by polymerization of said monomers, comprising:
   (a) precharging all of the slowest reacting monomer in an amount in accordance with the selected composition, optionally with part of one or more of said faster reacting monomers, and
   (b) introducing the faster reacting monomer or monomers independently and incrementally or continuously into the reactor at a specific feeding schedule for each monomer, as determined for each monomer before the polymerization by the following equations:

$$A_j(t) = \frac{1}{1+\exp\left[\frac{a_{1j} - \frac{a_{2j}}{2} - t}{a_{3j}}\right]} \left[1 - \frac{1}{1+\exp\left[\frac{a_{1j} + \frac{a_{2j}}{2} - t}{a_{4j}}\right]}\right] \quad \text{EQUATION 1}$$

where $A_j(t)$ has four adjustable parameters, $a_1$, $a_2$, $a_3$ and $a_4$ for each monomer:
and
$a_1$ determines the center of the distribution;
$a_2$ affects the width of the distribution;
$a_3$ determines the ascending portion of the distribution; and
$a_4$ determines the descending portion of the distribution; and
t=time in minutes during copolymerization;
and $$\% \text{ of Monomer } j \text{ charged at time } t_i = \frac{A_j(t_i)}{\sum_{t=0}^{N} A_j(t_i)} \times 100 \quad \text{EQUATION 2}$$

where
N=the overall time of the polymerization reaction;
wherein a set of determined values for $a_1$, a2, $a_3$ and $a_4$ provides said specific feeding schedule and assures that the curve of the rate of disappearance vs. time for the fastest reacting monomer substantially coincides with the rate of disappearance for each of the slower reacting monomer or monomers, as shown in FIG. 2 herein.

* * * * *